United States Patent
Rife et al.

(10) Patent No.: US 11,202,881 B2
(45) Date of Patent: Dec. 21, 2021

(54) CHEST-SUPPORTED NEBULIZER APPARATUS

(71) Applicants: Chaddi Rife, Danville, VA (US); Joshua Matthew Rife, Danville, VA (US)

(72) Inventors: Chaddi Rife, Danville, VA (US); Joshua Matthew Rife, Danville, VA (US)

( * ) Notice: Subject to any disclaimer, the term of this patent is extended or adjusted under 35 U.S.C. 154(b) by 431 days.

(21) Appl. No.: 16/403,040

(22) Filed: May 3, 2019

(65) Prior Publication Data

US 2019/0374740 A1    Dec. 12, 2019

Related U.S. Application Data

(60) Provisional application No. 62/681,190, filed on Jun. 6, 2018.

(51) Int. Cl.
*A61M 11/06*    (2006.01)
*A61M 16/14*    (2006.01)

(52) U.S. Cl.
CPC ............ *A61M 16/14* (2013.01); *A61M 11/06* (2013.01); *A61M 2209/088* (2013.01)

(58) Field of Classification Search
CPC .............................. A61M 11/00; A61M 11/06; A61M 2209/084; A61M 2209/088; A61M 16/14; A61M 16/16; A61M 2210/10
See application file for complete search history.

(56) References Cited

U.S. PATENT DOCUMENTS

| | | | |
|---|---|---|---|
| 7,013,894 B2 | 3/2006 | McFarland, Jr. | |
| 7,322,349 B2 | 1/2008 | Power | |
| 9,126,005 B1* | 9/2015 | Blaylock | A62B 18/08 |
| 9,180,262 B2 | 11/2015 | Cota et al. | |
| 9,724,483 B2 | 8/2017 | Hyde et al. | |
| 2008/0066747 A1* | 3/2008 | Spink | A61M 11/06 |
| | | | 128/202.13 |
| 2013/0306060 A1* | 11/2013 | Cota | A61M 15/00 |
| | | | 128/200.14 |
| 2015/0007810 A1* | 1/2015 | Smith | A61M 15/00 |
| | | | 128/200.14 |
| 2015/0007812 A1* | 1/2015 | Smith | A61M 15/00 |
| | | | 128/200.21 |
| 2017/0100304 A1* | 4/2017 | Venkataraya | A61M 15/0021 |
| 2019/0247599 A1* | 8/2019 | Lee | A61M 11/06 |

* cited by examiner

*Primary Examiner* — Joseph D. Boecker
(74) *Attorney, Agent, or Firm* — Boudwin Intellectual Property; Daniel Boudwin

(57) ABSTRACT

A chest-supported nebulizer apparatus. The chest-supported nebulizer apparatus has a planar base that rests on the chest of a user. At least one lateral strap and a neck strap is removably securable from the planar base. The neck strap can encircle the neck of the user and is slidably adjustable to adjust the length of the neck strap. A receptacle is disposed in the planar base, wherein the receptacle can receive a central support therein. The central support is pivotally affixed to the receptacle, allowing a user to adjust the angle of the central support relative to the planar base. A support assembly is slidably affixed to the central support. The support assembly is sized to receive a nebulizer.

18 Claims, 9 Drawing Sheets

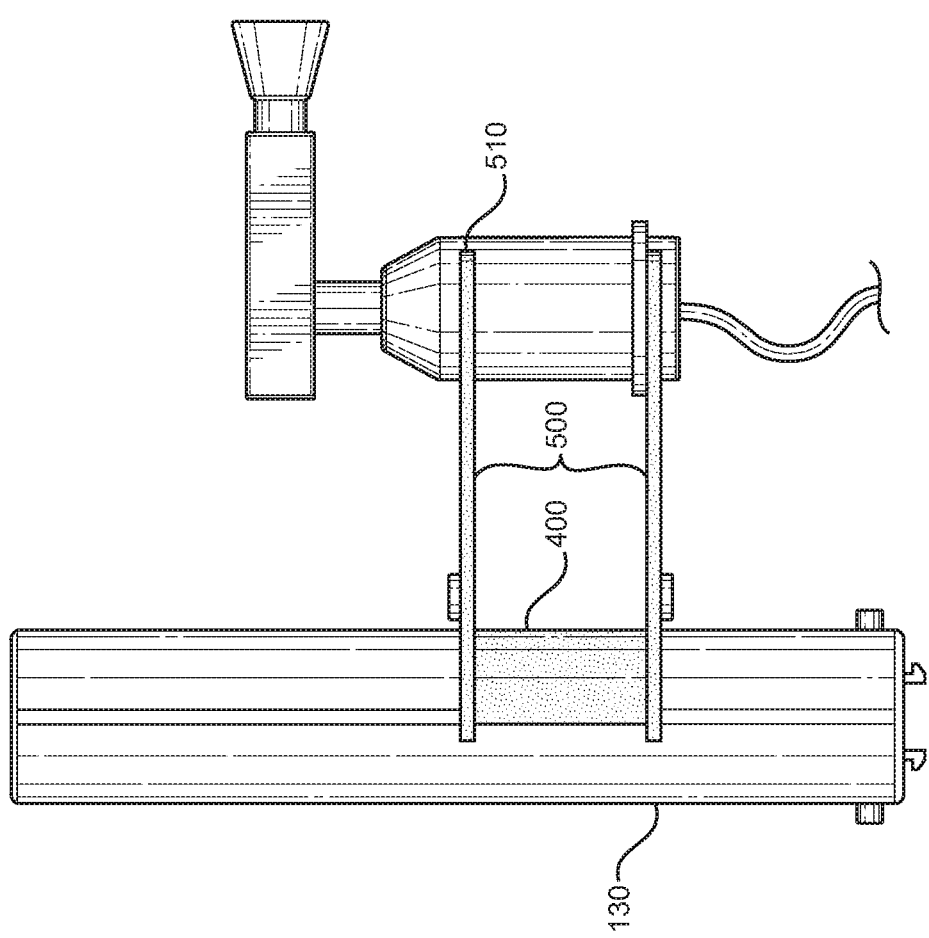

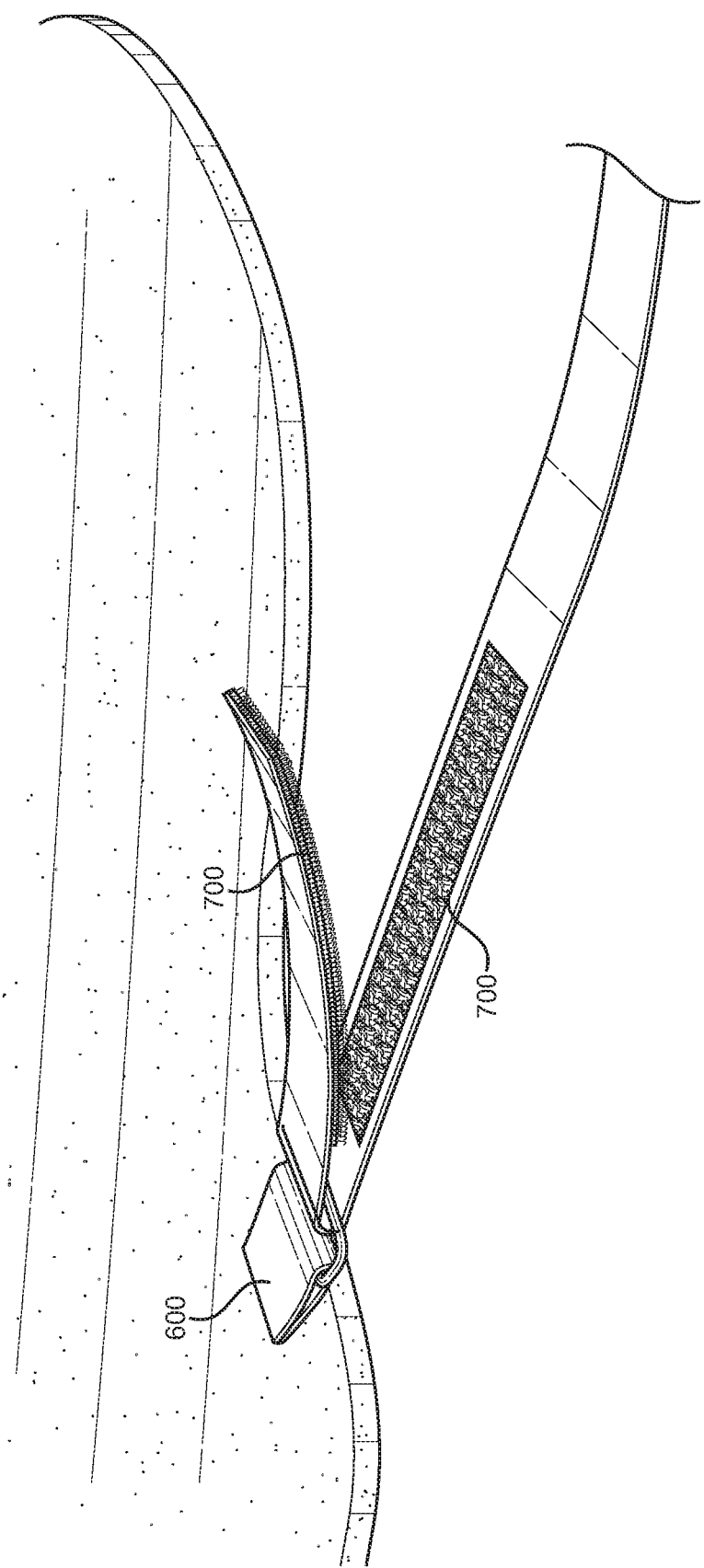

CHEST-SUPPORTED NEBULIZER APPARATUS

CROSS REFERENCE TO RELATED APPLICATIONS

This application claims the benefit of U.S. Provisional Application No. 62/681,190 filed on Jun. 6, 2018. The above identified patent application is herein incorporated by reference in its entirety to provide continuity of disclosure.

BACKGROUND OF THE INVENTION

The present invention relates to support structures for nebulizers. More particularly, the present invention provides for a chest-supported nebulizer apparatus wherein a base removably secures a support with an adjustable arm adapted to receive a nebulizer, such that a user can position a nebulizer at a desired height and angle.

Many individuals suffer from asthma, cystic fibrosis, chronic obstructive pulmonary disease or other respiratory diseases and disorders. In order to combat these illnesses, a medical device known as a nebulizer is used to administer medication in the form of a mist that is delivered through an individual's mouth or nose into the lungs. Proper use of a nebulizer requires that the device be held in an upright position in order to prevent spilling and promote the nebulization of the medication. Keeping the nebulizer in such a position may be difficult, or even impossible, where an individual is struggling with limited mobility or paralysis. Accordingly, a chest-supported nebulizer apparatus wherein a base removably secures a support with an adjustable arm adapted to receive a nebulizer, such that a user can position the nebulizer at a desired height and angle to maintain the proper position of the nebulizer is desired.

The present invention substantially diverges in design elements from the known art and consequently it is clear that there is a need in the art for an improvement to existing support structures for nebulizers. In this regard the present invention substantially fulfills these needs.

SUMMARY OF THE INVENTION

In view of the foregoing disadvantages inherent in the known types of support structures for nebulizers now present in the art, the present invention provides a chest-supported nebulizer apparatus wherein a base removably secures a support with an adjustable arm adapted to receive a nebulizer wherein the same can be utilized for providing convenience to the user by allowing the user to position the nebulizer at a desired height and angle to maintain the proper position of the nebulizer.

The present chest-supported nebulizer apparatus comprises a planar base adapted to rest on the chest of a user. At least one lateral strap is removably securable from the planar base. A neck strap is also removably securable to the planar base. The neck strap is configured to encircle a neck of the user and is slidably adjustable to adjust the length of the neck strap. A receptacle is disposed in the planar base, configured to receive a central support. The central support is pivotally affixed to the receptacle, configured to adjust the angle of the central support relative to the planar base. A support assembly is slidably affixed to the central support. The support assembly is configured and sized to receive a nebulizer.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 5 shows a side view of an embodiment of the chest-supported nebulizer apparatus.

FIG. 7A shows a close-up view of the neck strap and lateral strap attachment mechanisms in an embodiment of the chest-supported nebulizer apparatus.

DETAILED DESCRIPTION OF THE INVENTION

Figure 1:
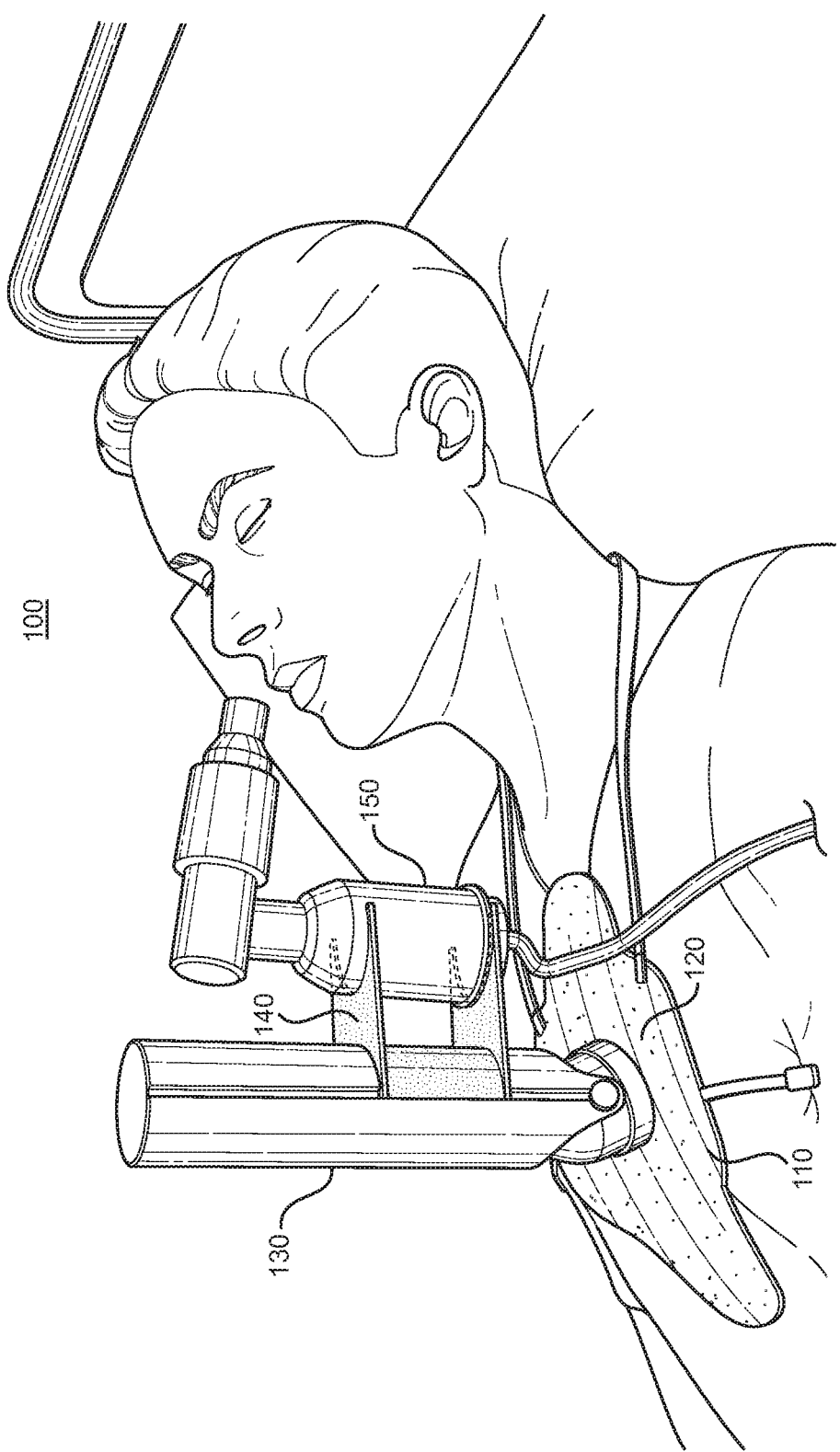
FIG. 1 shows a perspective view of an embodiment of the chest-supported nebulizer apparatus in use.

Reference is made herein to the attached drawings. Like reference numerals are used throughout the drawings to depict like or similar elements of the chest-supported nebulizer apparatus. For the purposes of presenting a brief and clear description of the present invention, a preferred embodiment will be discussed as used for the chest-supported nebulizer apparatus. The figures are intended for representative purposes only and should not be considered to be limiting in any respect.

Referring now to FIG. 1, there is shown a perspective view of an embodiment of the chest-supported nebulizer apparatus in use. The chest-supported nebulizer apparatus 100 comprises a planar base 110, a receptacle 120 disposed in the planar base 110 that is configured to receive a removably securable central support 130, and a support assembly 140 slidably affixed to the central support 130. The chest-supported nebulizer apparatus 100 is configured to enable the dispensing of a medication through a nebulizer 150, wherein the nebulizer 150 is secured to a user without the need for the user to stabilize or hold the nebulizer device.

The planar base 110 is configured to rest on the chest of a user. In the shown embodiment, the planar base 110 is sized and shaped to rest on the chest of a young adult, however other sizes and shapes of the planar base 110 are contemplated by this disclosure, and it is contemplated by this disclosure that the planar base 110 will be sized and shaped to fit the body type and shape of the user. In the preferred embodiment, the planar base 110 is comprised of a soft, non-slip material to prevent the planar base 110 from sliding along the chest of the user. In one embodiment, the planar base 110 comprises a flexible material such that the planar base 110 conforms to the shape of the user's chest. In another embodiment, the planar base 110 comprises a padded material to provide further comfort to the user.

Figure 2:
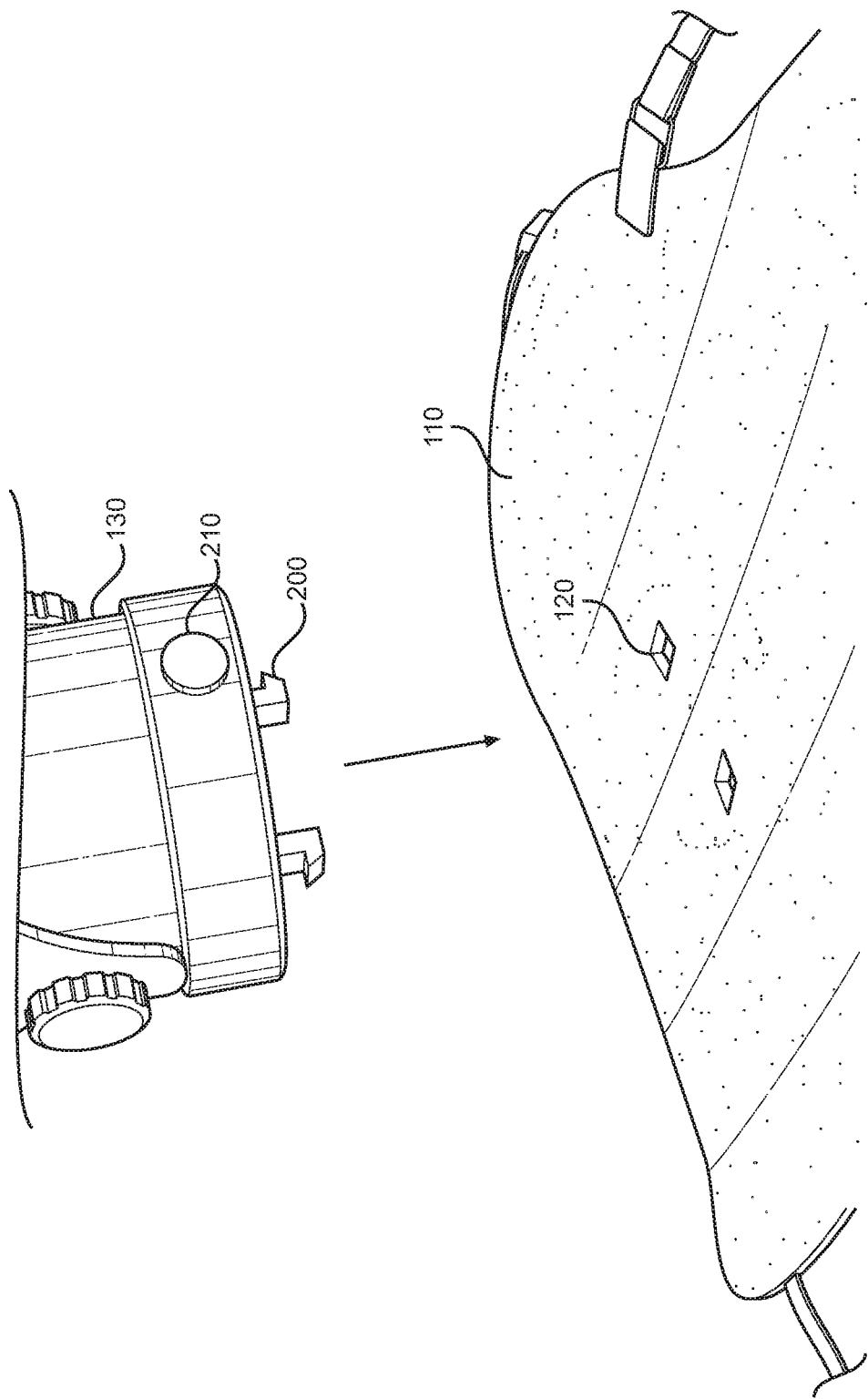
FIG. 2 shows a close-up view of the attachment mechanism in an embodiment of the chest-supported nebulizer apparatus.

Referring now to FIG. 2, there is shown a close-up view of the attachment mechanism in an embodiment of the chest-supported nebulizer apparatus. In the shown embodiment, the receptacle 120 is in the form of a pair of square shaped apertures disposed in the center of the planar base 110 configured to receive a pair of interlocking posts 200 disposed on the underside of the removably securable central support 130. As further shown in the embodiment, a releasing button 210 is disposed on the lower lateral surface of the removably securable central support 130 that is configured to release the pair of interlocking posts 200 on the lower end of the central support 130 from the receptacle 120 when depressed.

Figure 3:
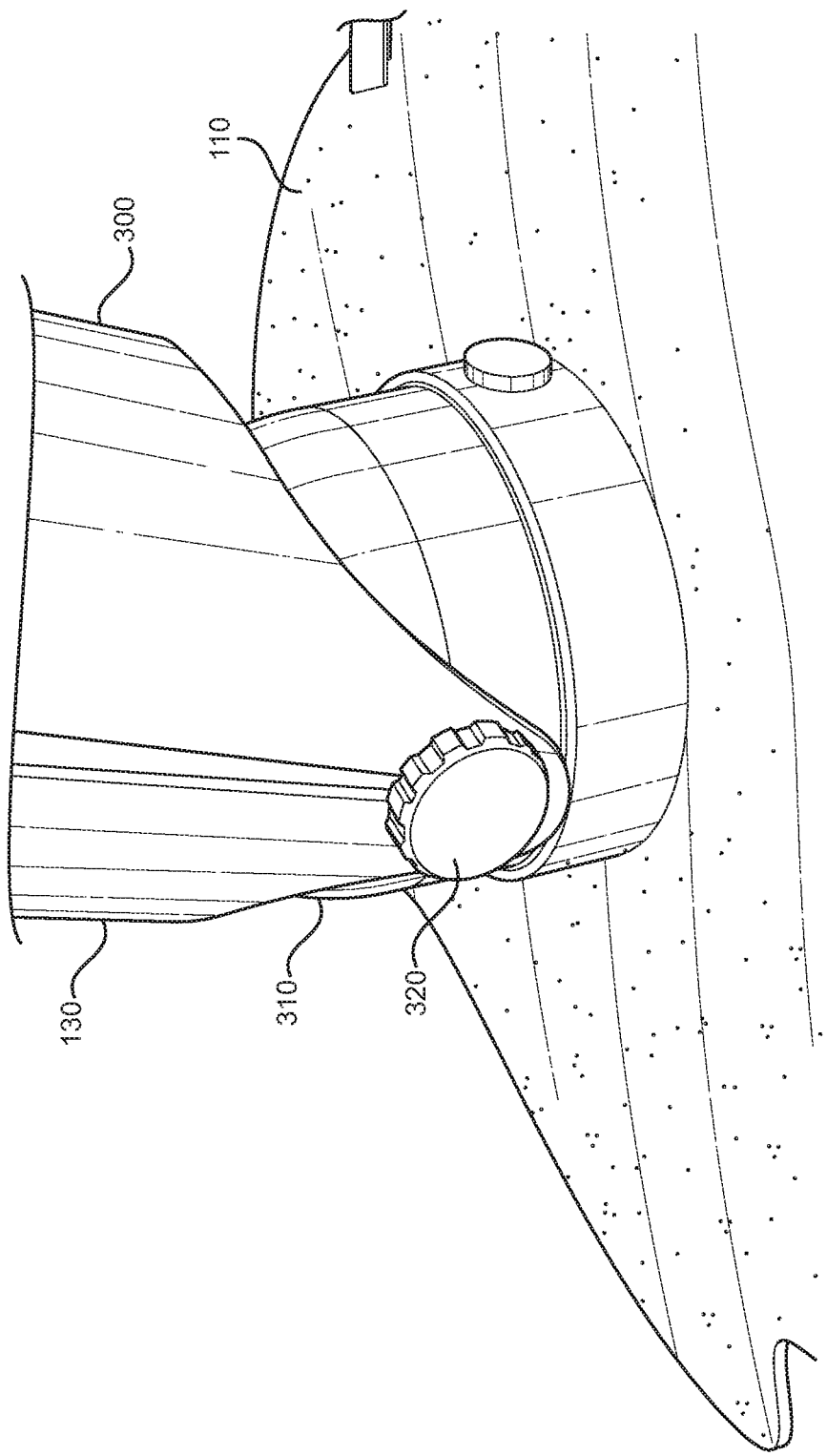
FIG. 3 shows a close-up view of the bottom portion of the support assembly in an embodiment of the chest-supported nebulizer apparatus.
Figure 4A:
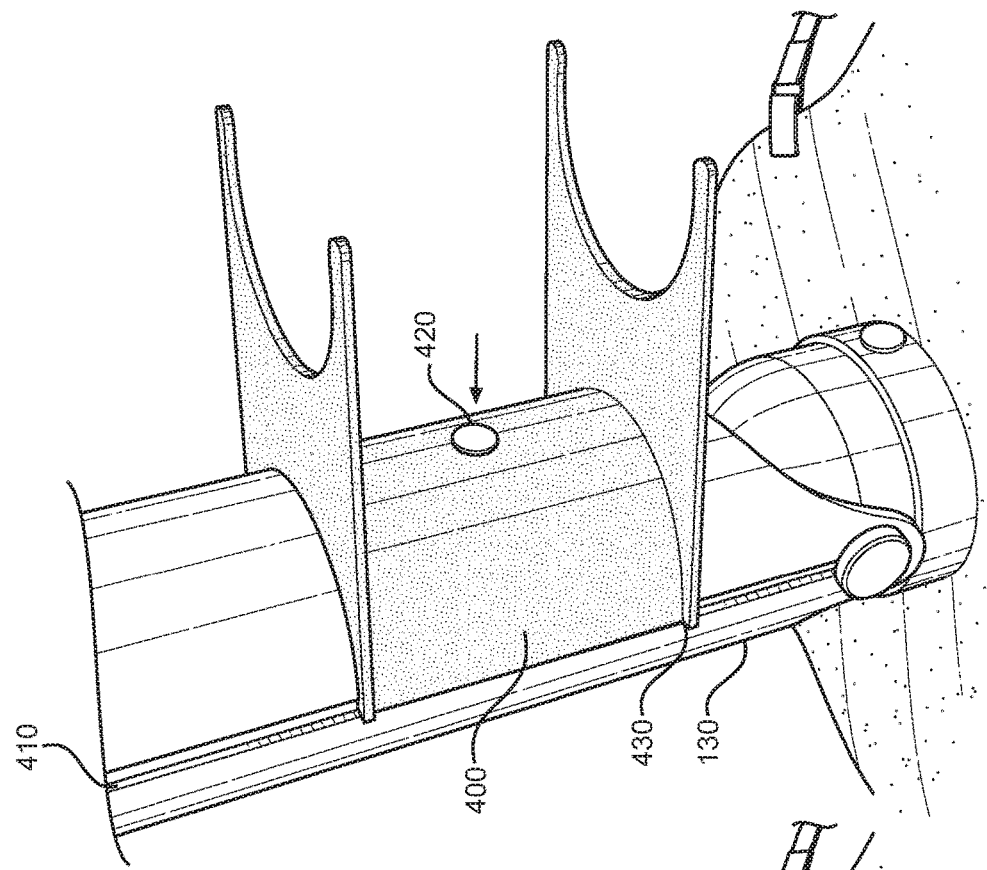
FIG. 4A shows a close-up view of the support assembly in an embodiment of the chest-supported nebulizer apparatus.
Figure 4B:
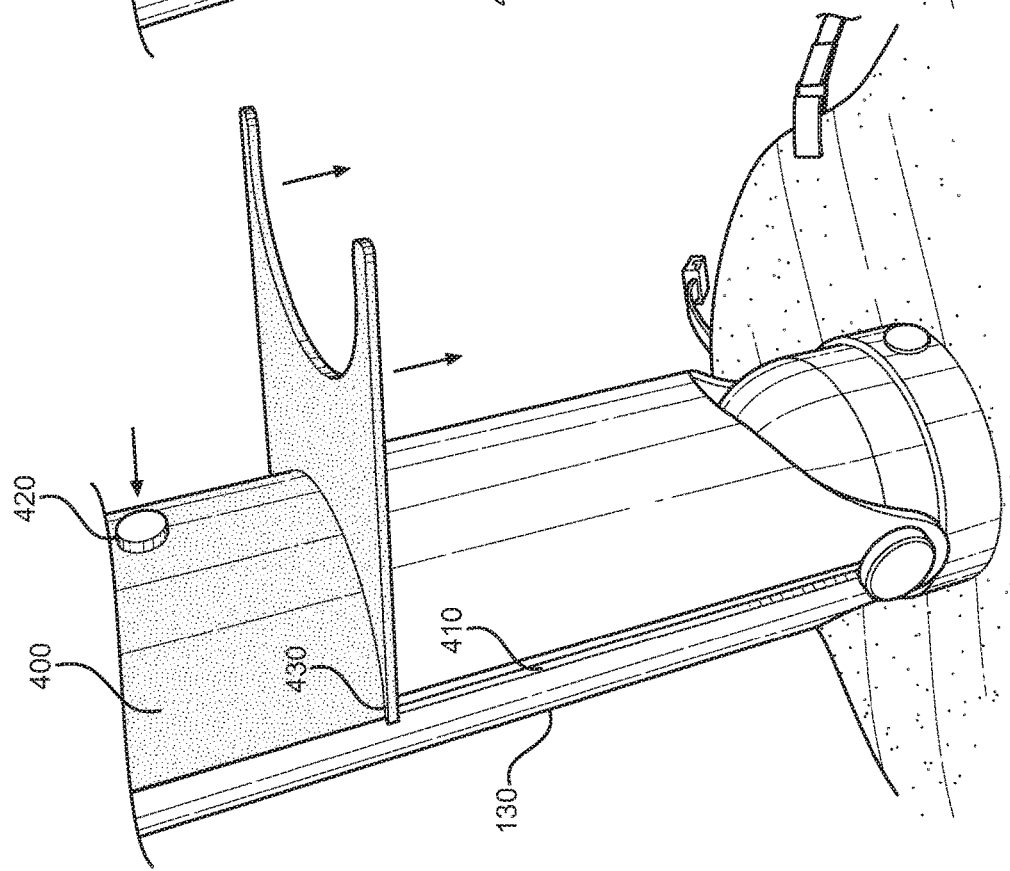
FIG. 4B shows a close-up view of the support assembly in an embodiment of the chest-supported nebulizer apparatus.
Figure 4C:
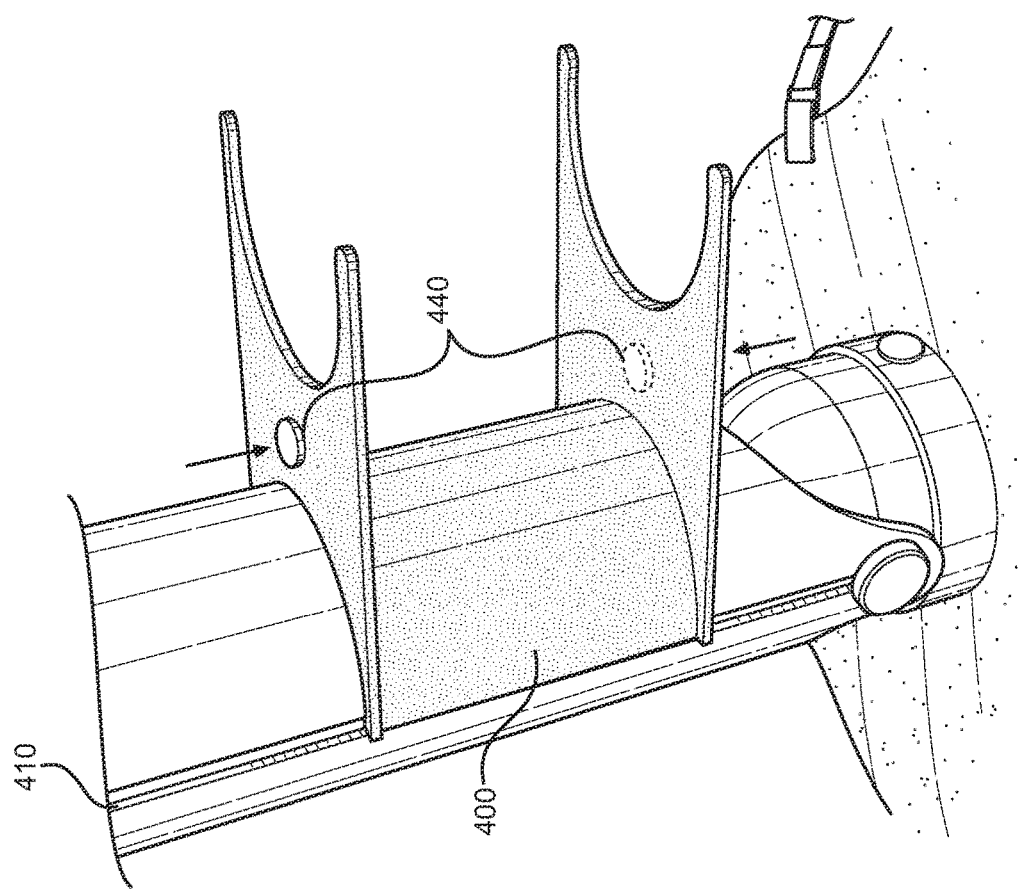
FIG. 4C shows a close-up view of the support assembly in an embodiment of the chest-supported nebulizer apparatus.
Figure 6:
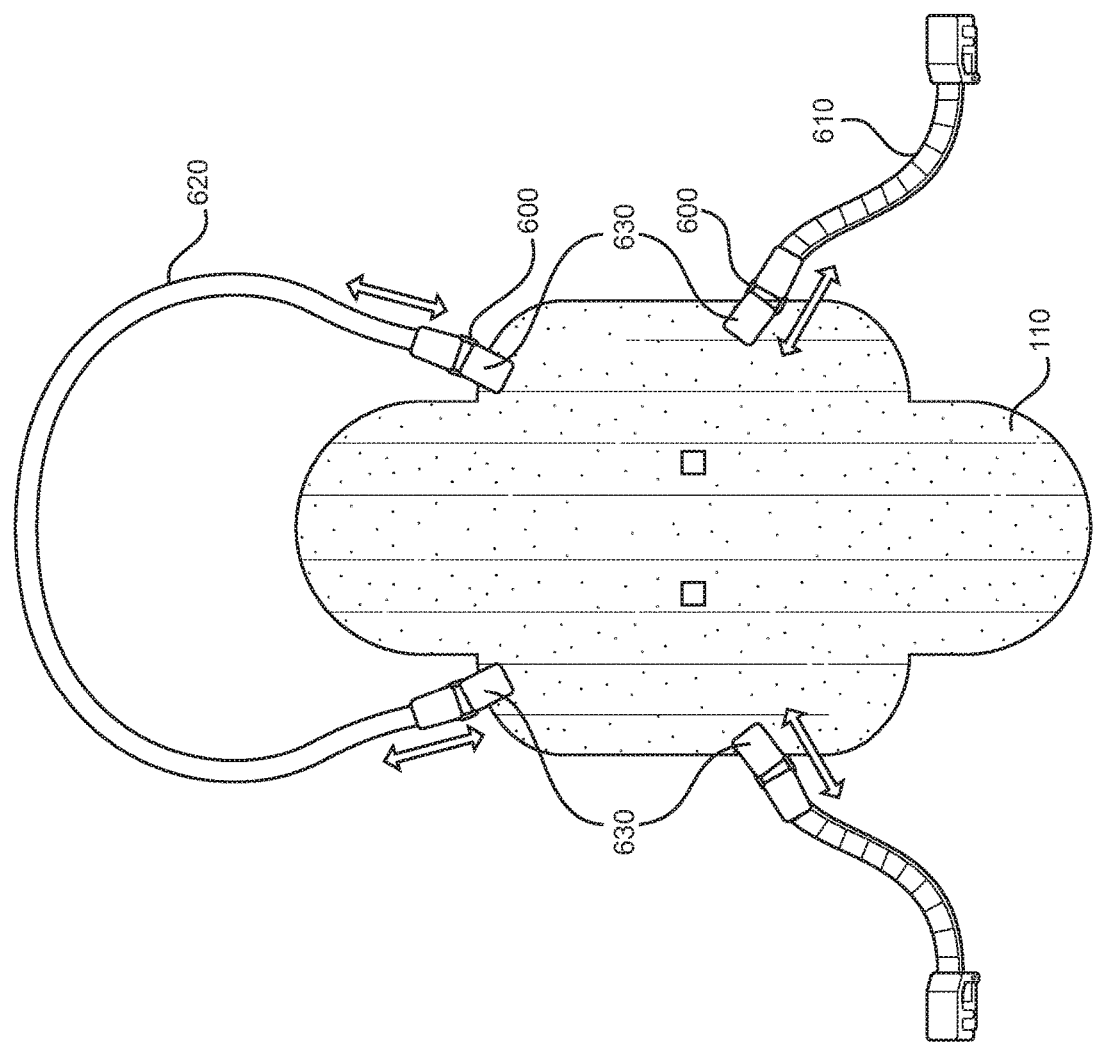
FIG. 6 shows a top-down view of an embodiment of the chest-supported nebulizer apparatus.
Figure 7B:
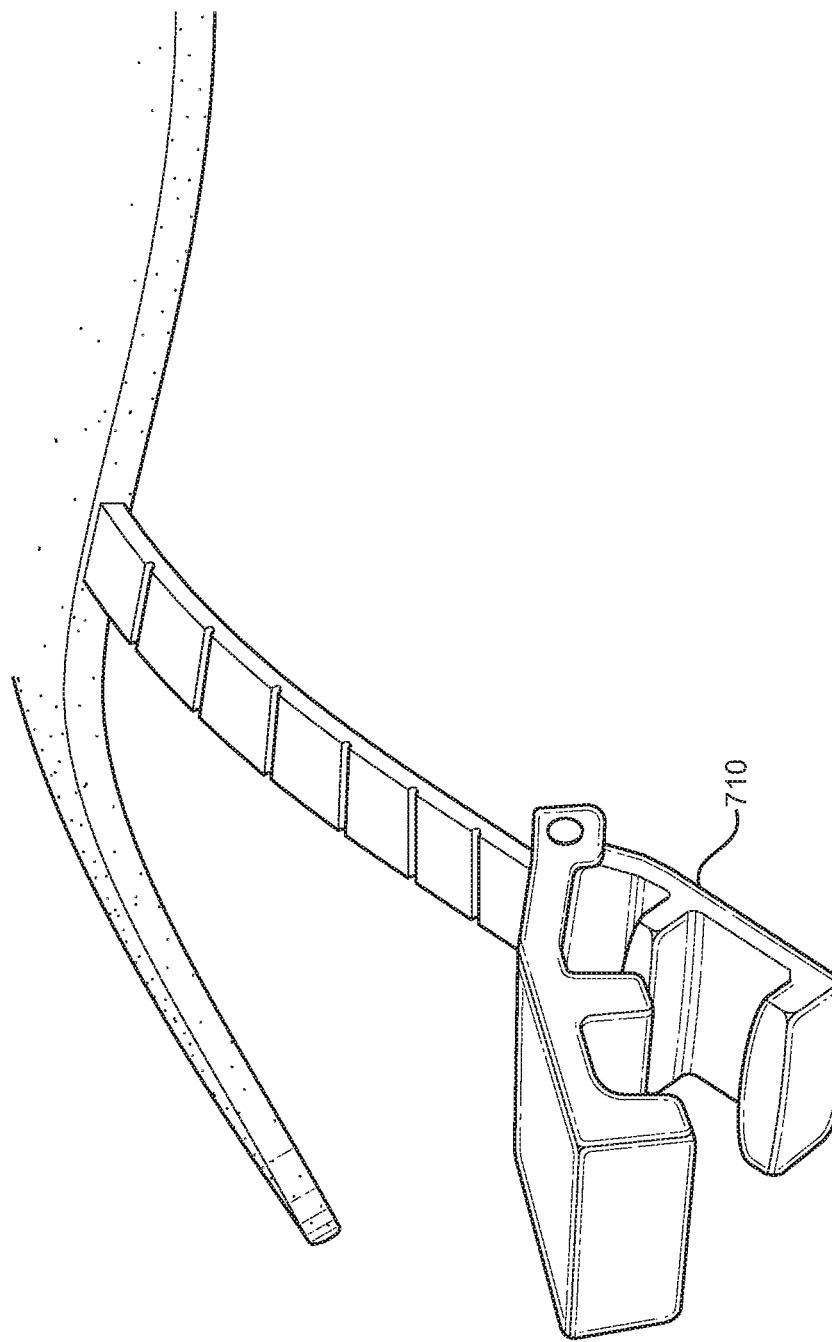
FIG. 7B shows a close-up view of the neck strap and lateral strap attachment mechanisms in an embodiment of the chest-supported nebulizer apparatus.

Referring now to FIG. 3, there is shown a close-up view of the bottom portion of the support assembly in an embodiment of the chest-supported nebulizer apparatus. The central support 130 is pivotally affixed to the receptacle and configured to adjust the angle of the central support 130 relative to the planar base 110. In the shown embodiment, the central support 130 is comprised of an elongated member 300 disposed on a ball joint 310. In the shown embodiment, a pivotal screw fastener 320 is disposed on the bottom portion of the central support, configured to lock and unlock the position of the elongated member 300 along the ball joint 310 thereby adjusting the angle of the central support 130 relative to the planar base 110. In this way, the user can selectively position and secure the elongated member 300 in a desired position. It should be understood by one of ordinary skill in the art that that any manner of attaching the central support 130 to the receptacle 120 providing the user the ability to adjust the angle of attachment will be included as a part of this disclosure including, but not limited to, a hinge.

Referring now to FIGS. 4A, 4B and 4C, there are shown close-up views of the support assembly in various embodiments of the chest-supported nebulizer apparatus. The support assembly 400 is slidably affixed to the central support 130 to adjust the height of an attached nebulizer. In the shown embodiments, the support assembly 400 is slidably affixed to the central support 130 via a tongue-in-groove system. A groove 410 runs the length of the central support 130 configured to receive a tongue component 430 disposed on the support assembly 400. In the embodiments shown in FIG. 4A and FIG. 4B, a push button 420 is disposed on the support assembly 400 which is configured to lock the position of the support assembly 400 in the groove 410. In another embodiment, shown in FIG. 4C, two squeeze buttons 440 are compressed to release the lock of the position of the support assembly 400 in order to allow the support assembly 400 to freely travel along the groove 410. It is contemplated that different configurations of the slidably affixed mechanism are possible and embody the present invention.

Referring now to FIG. 5, there is shown a side view of an embodiment of the chest-supported nebulizer apparatus. The support assembly 400 is configured to receive a nebulizer device. In the shown embodiment the support assembly 400 is composed of a longitudinally opposing pair of lateral panels 500 disposed perpendicular to the central support 130. The lateral panels 500 comprise a cutout 510 dimensioned to receive a nebulizer. In the shown embodiment the cutouts 510 comprise an arcuate shape configured to receive a nebulizer by friction fit. In another embodiment the support assembly 400 can comprise a system of platforms and contoured cutouts 510 on which a nebulizer can rest. One of ordinary skill in the art will understand that any manner of receiving a nebulizer on the support assembly is also contemplated as part of this disclosure.

Referring now to FIG. 6, there is shown a top-down view of an embodiment of the chest-supported nebulizer apparatus. In the shown embodiment, connection rings 600 are disposed along lateral protrusions 630 disposed along the perimeter of the planar base 110. In one embodiment, the lateral protrusions are flexible thereby allowing the planar base 110 to follow the contours of the user's chest and drape over the sides of the user's chest, thereby allowing the planar base 110 to conform to the shape of the user's torso. In the shown embodiment two lateral straps 610 and a neck strap 620 are removably secured to the planar base 110 via the connection rings 600. The lateral straps 610 are configured to loop through the connection rings 600 and the lateral straps 610 are adjustable in length and dimensioned to be long enough to encircle the torso of the user. In another embodiment, the lateral straps 610 are adjustable in length and dimensioned to be long enough to secure the planar base 110 to a stretcher, wheelchair, or other suitable surface. The neck strap 620 is also configured to loop through the connection rings 600 and the neck strap 620 is adjustable and is dimensioned to be long enough to encircle the neck of the user.

Referring now to FIGS. 7A and 7B, there are shown a close-up view of the neck strap and lateral strap attachment mechanisms in an embodiment of the chest-supported nebulizer apparatus. In the shown embodiment two lateral straps 610 and a neck strap 620 are removably secured to the planar base 110 via the connection rings 600. In the embodiment shown in FIG. 7A the lateral straps and the neck strap comprise a hook and look mechanism 700 disposed on both the proximate and distal ends of the straps. In such an embodiment the proximate end of the straps can be passed through the connection rings 600 and secured in place. The length of the straps are selectively adjustable and the distal ends of the straps are secured to a receiving structure, such as a ring, or secured about a support structure such as around the leg of a hospital bed. In the embodiment shown in FIG. 7B, the lateral straps and the neck strap are secured via a clamp mechanism 710 disposed on the distal end of the straps. One of ordinary skill in the art will understand that any manner of securing the lateral straps and the neck strap to a suitable surface are also contemplated by this disclosure.

In use, the chest-supported nebulizer apparatus can maximize nebulization of the medication and delivery of the medication through the nose and/or mouth of the user to the user's lungs without the need for the user to hold or stabilize the device. The planar base can be placed on a user's chest. One end of the neck strap is secured to the planar base and the opposite end is passed behind the user's head and secured to the planar base. In such a manner, the user's head is encircled by the neck strap. Lateral straps are secured to the planar base and the length of the straps adjusted such that the lateral straps are secured to a support structure. In such a manner, the planar base is be firmly secured in place on a user's chest such that the planar base conforms to the contours of the user's chest and will not move.

The central support is secured to the planar base via the receiving receptacle. A support assembly can be slidably adjusted via a tongue and groove mechanism to adjust the height of the support assembly. A nebulizer can be secured in the support assembly, and by adjusting the angle of the central support and the height of the support assembly the nebulizer can be positioned at the optimal height and angle to maximize delivery of the medication through the nose and/or mouth of the user to the user's lungs without the need for the user to hold or stabilize the device.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A chest-supported nebulizer apparatus, comprising:

a planar base adapted to rest on a chest of a user;

wherein at least one lateral strap is removably securable to an opposing lateral edge of the planar base;

wherein a neck strap is removably securable to an upper edge of the planar base;

wherein the neck strap is configured to secure around a neck of the user;

wherein the neck strap is slidably adjustable to adjust the length of the neck strap;

a receptacle disposed on the upper edge of the planar base, configured to removably receive a central support;

wherein the central support is comprised of a first end and a second end;

wherein the first end of the support is comprised of an interlocking mechanism configured to be received by the receptacle;

wherein the central support is pivotally affixed to the receptacle and is configured to adjust an angle of the central support relative to the planar base;

a support assembly slidably affixed to the central support;

wherein the support assembly is configured to removably secure a nebulizer therein.

2. The chest-supported nebulizer apparatus of claim 1, wherein the at least one lateral strap is configured to secure to a support structure.

3. The chest-supported nebulizer apparatus of claim 1, wherein the at least one lateral strap is configured to encircle a torso of the user.

4. The chest-supported nebulizer apparatus of claim 1, wherein the central support is pivotable about a hinge disposed on a lower end thereof, wherein the hinge comprises a pivotal screw fastener configured to selectively pivot the central support to a desired position.

5. The chest-supported nebulizer apparatus of claim 1, wherein the at least one lateral strap comprises a latch on a distal end thereof, wherein the latch is removably securable to a support structure.

6. The chest-supported nebulizer apparatus of claim 1, wherein the neck strap further comprises a hook and loop fastener.

7. The chest-supported nebulizer apparatus of claim 1, wherein the lateral strap further comprises a hook and loop fastener.

8. The chest-supported nebulizer apparatus of claim 5, wherein the latch is adjustable along the respective strap on which it is disposed via a hook and loop fastener.

9. The chest-supported nebulizer apparatus of claim 1, wherein the support assembly comprises a cutout dimensioned to receive a nebulizer therein.

10. The chest-supported nebulizer apparatus of claim 1, wherein the cutout comprises an arcuate shape.

11. The chest-supported nebulizer apparatus of claim 1, wherein the support assembly is slidably affixed to the central support via a tongue and groove system.

12. The chest-supported nebulizer apparatus of claim 11, wherein the position of the support assembly along the central support is locked in place and released via a push button release system.

13. The chest-supported nebulizer apparatus of claim 1, wherein the central support is comprised of an elongated member disposed on a ball joint.

14. The chest-supported nebulizer apparatus of claim 1, wherein the planar base comprises a plurality of protrusions on either side thereof.

15. The chest-supported nebulizer apparatus of claim 14, wherein the at least one lateral strap removably secures to the plurality of protrusions.

16. The chest-supported nebulizer apparatus of claim 1, wherein an underside of the planar base comprises a non-slip material.

17. The chest-supported nebulizer apparatus of claim 1, wherein a plurality of connection rings are disposed along a plurality of lateral protrusions disposed along the perimeter of the planar base.

18. The chest-supported nebulizer apparatus of claim 17, wherein the plurality of connection rings are configured to receive strap therethrough.

* * * * *